United States Patent [19]

Kluge et al.

[11] 4,431,665
[45] Feb. 14, 1984

[54] ACYLATED LAIDLOMYCIN DERIVATIVES

[75] Inventors: Arthur F. Kluge, Los Altos; Robin D. Clark, Palo Alto, both of Calif.

[73] Assignee: Syntex (U.S.A.) Inc., Palo Alto, Calif.

[21] Appl. No.: 162,473

[22] Filed: Jun. 24, 1980

Related U.S. Application Data

[63] Continuation-in-part of Ser. No. 65,812, Aug. 13, 1979, abandoned.

[51] Int. Cl.[3] .................... A61K 31/35; C07D 309/10
[52] U.S. Cl. .................................. 424/283; 549/343
[58] Field of Search ....................... 424/283; 549/343

[56] References Cited

U.S. PATENT DOCUMENTS 3,794,732  2/1974  Raun .................................. 424/283

Primary Examiner—Frederick E. Waddell
Attorney, Agent, or Firm—James M. Kanagy; Tom M. Moran

[57] ABSTRACT

Compounds represented by the formula (A)

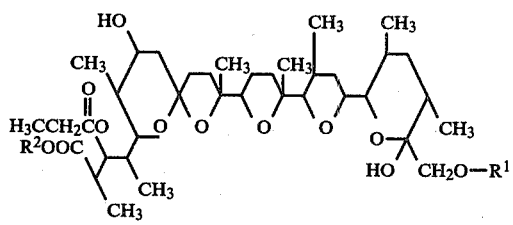

wherein $R^1$ is an aliphatic or alicyclic hydrocarbon acyl group of two to eighteen carbon atoms and $R^2$ is an alkali metal cation or hydrogen are useful for increasing the feed efficiency of ruminants and for treating coccidiosis in domestic animals, especially chickens.

14 Claims, No Drawings

ACYLATED LAIDLOMYCIN DERIVATIVES

This application is a continuation-in-part of Ser. No. 65,812, filed Aug. 13, 1979, now abandoned.

BACKGROUND OF THE INVENTION

1. Field of the Invention

This invention relates to novel esters of laidlomycin

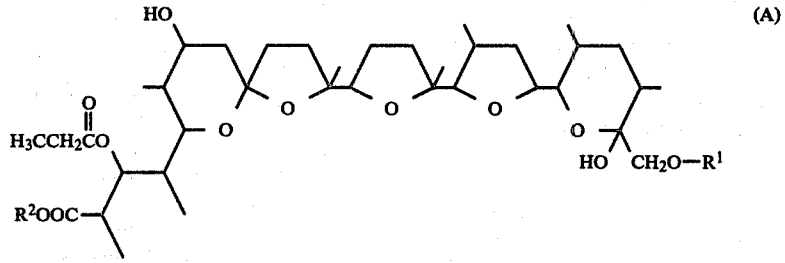

which are used to increase the feed efficiency in ruminants and to treat coccidiosis in domestic animals, especially in chickens.

2. Prior Art

The antibiotic laidlomycin is a known compound which inhibits the growth of some Gram-positive bacteria. See *The Journal of Antibiotics,* Vol. XXIX, No. 7, pp. 759–761, July, 1976 and Vol. XXVII, No. 11, pp. 884–888, Nov. 1974. Monensin is also a known antibiotic and has been shown to be useful in increasing feed utilization in ruminants. See for example, U.S. Pat. No. 3,794,732. The structure of each of these compounds is shown in Formula (I), below, wherein for laidlomycin R is propionate and A is hydrogen, for monensin (Factor A) R is methoxy and A is methyl, and for monensin (Factor B) R is methoxy and A is hydrogen.

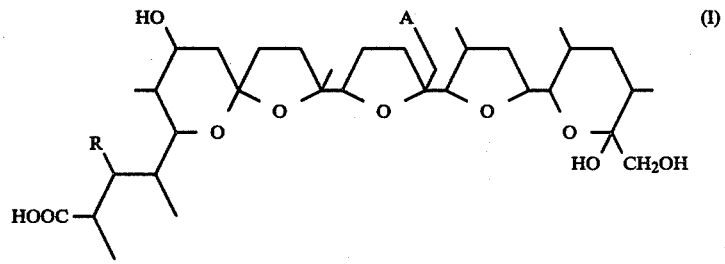

As discussed in the above-mentioned U.S. Pat. No. 3,794,732, it is important to increase the efficiency of feed utilization in domestic animals, especially meat producing and milk producing animals such as cattle. Carbohydrates form a large part of these animals' diets, and the efficiency of carbohydrate utilization is desirably increased by treatments which encourage intraruminal production of propionate rather than acetate from the carbohydrates. The theory behind this is discussed in the '732 patent and is incorporated herein by reference.

The improved efficiency of feed utilization resulting from the use of compounds described by Formula (I), above, can be determined by observing an increased concentration or molar percentage of propionate in the rumen.

Surprisingly, it has now been discovered that the laidlomycin esters of this invention exhibit an unexpectedly superior increase in the molar percentage of propionate produced by rumen microorganisms as compared to laidlomycin or the sodium salt thereof. It has also been found that the compounds of this invention inhibit lactic acid production better than laidlomycin or its sodium salt.

SUMMARY OF THE INVENTION

One aspect of this invention is a compound chosen from those represented by the formula wherein $R^1$ is an aliphatic or alicyclic hydrocarbon acyl group of 2 through 18 carbon atoms and $R^2$ is hydrogen or an alkali metal cation (e.g. sodium, potassium or lithium).

Another aspect of the invention is the combination of a compound chosen from those represented by Formula (A), above, wherein $R^1$ and $R^2$ are as defined, with a suitable feed carrier for a ruminant animal.

A further aspect of this invention is a process for increasing the efficiency of feed utilization of an animal having a developed rumen function (a ruminant) which comprises orally administering to such animal a feed efficiency increasing amount of at least one compound represented by Formula (A) above, wherein $R^1$ and $R^2$ are as defined hereinabove.

Still another aspect of this invention is a method for controlling coccidial infections in a warm blooded animal host having need for such treatment which comprises administering an anticoccidially effective amount of a compound of Formula (A), above, wherein $R^1$ and $R^2$ are as defined above.

Still another aspect of this invention is a veterinary composition which comprises at least one compound represented by Formula (A) above (where $R^1$ and $R^2$ are as defined) and a veterinary pharmaceutically acceptable excipient.

Still another aspect of this invention is a process for preparing a compound represented by Formula (A) wherein $R^1$ and $R^2$ are as defined above, which process comprises reacting a compound of Formula (A) wherein $R^1$ is hydrogen and $R^2$ is as defined previously with a reactive derivative of an aliphatic hydrocarbon acid of two through eighteen carbons at temperatures of 0° to 30° C. Preferred reaction times are less than 10 hours.

FURTHER DISCUSSION AND DESCRIPTION OF PREFERRED EMBODIMENTS

The compounds of this invention include those compounds of Formula (A) wherein $R^2$ is hydrogen or an alkali metal salt and $R^1$ is an aliphatic or alicyclic hydrocarbon acyl group of two through eighteen carbon atoms. Each ester is derived from a reactive derivative of the corresponding acid containing 2 to 18 carbon atoms, i.e. straight chain, branched or cyclic aliphatic hydrocarbons. Thus, representative aliphatic $R^1O$- groups are, inter alia, acetate, propionate, butyrate, valerate, hexanoate, heptanoate, octanoate, nonanoate, decanoate, undecanoate, dodecanoate, tridecanoate, tetradecanoate, hexadecanoate, heptadecanoate, stearate or various branched alkanoates. Representative alicyclic $R^1O$- groups are cycloalkyl carboxylate moieties such as cyclopropylcarboxylate, cyclobutylcarboxylate, cyclopentylcarboxylate, cyclohexylcarboxylate, cycloheptylcarboxylate, cyclooctylcarboxylate or the like.

Of these esters, the alkanoates of 3-6 carbon atoms are preferred while alkanoates of 3 or 4 carbon atoms are particularly preferred, the butyrate being the most preferred compound.

The monoester compounds of the invention are readily prepared by reacting laidlomycin or an alkali metal salt thereof at low temperatures such as about 0°–30° C. with a suitable derivative of an alkanoic acid such as a suitable acid halide, e.g. an acid chloride, or an anhydride, for example acetyl chloride,
    propionyl chloride,
    butyryl chloride,
    valeryl chloride,
    hexanoyl chloride,
    heptanoyl chloride,
    octanoyl chloride,
    nonanoyl chloride,
    decanoyl chloride,
    undecanoyl chloride,
    dodecanoyl chloride,
    stearyl chloride,
    cyclopropylcarboxylic chloride,
    cyclobutylcarboxylic chloride,
    cyclopentylcarboxylic chloride,
    cyclohexylcarboxylic chloride,
    the anhydrides corresponding to the above acid chlorides, (particularly the symmetric acid anhydrides) and the like.

The reaction is carried out in a suitable inert solvent, preferably a cyclic amine such as pyridine. Generally the reaction is finished in less than 10 hours, 3 hours being needed at 5° C. for the formation of the butyrate. It is preferred to employ between 1 and 2 moles of acid halide per mol of laidlomycin, or the employ between 1 and 2 moles of acid anhydride per mole of laidlomycin.

Administration of a compound of this invention results in improved food utilization and also prevents and treats ketosis, the abnormal increase of ketones in the body. The causative mechanism of ketosis is a deficient production of propionate compounds. A presently recommended treatment is administration of propionic acid or feeds which preferentially produce propionate. Because the compounds of this invention encourage propionate production from ordinary feeds, feed efficiency is increased and the incidence of ketosis is reduced.

The compounds of this invention are most readily administered orally to the ruminants to be treated. The easiest way to administer the compounds is merely by mixing them with a suitable feed carrier and feeding the animals this animal feed.

However, the compounds can be usefully administered in other ways. For example, they can be combined with a suitable, non-toxic veterinary pharmaceutical excipient incorporated into tablets, drenches, boluses or capsules and dosed to the animals. Formulation of the compounds of this invention in such dosage forms can be accomplished by means or methods well known in the veterinary pharmaceutical art. Each individual dosage unit should contain a quantity of the feed efficiency improving compound which has a direct relation to the proper daily dose of the animals to be treated.

Capsules are readily produced by filling gelatin capsules with any desired form of the desired compound alone or diluted with a pharmaceutical excipient such as an inert powdered kiluent, e.g. sugar, starch or purified crystalline cellulose in order to increase its volume for convenience in filling capsules.

Tablets of the compounds of this invention are made by conventional pharmaceutical processes. Manufacture of tablets is a well known and highly advanced art. In addition to the active ingredient, a tablet usually contains other pharmaceutical excipients such as a base, a disintegrator, an absorbant, a binder, and a lubricant. Typical bases include lactose, fine icing sugar, sodium chloride, starch and mannitol. Starch is also a good disintegrator as is alginic acid. Surface active agents such as sodium lauryl sulfate and dioctyl sodium sulfosuccinate are also used. Commonly used absorbants again include starch and lactose while magnesium carbonate is also useful for oily substances. Frequently used binders are gelatin, gums, starch, dextrin and various cellulose derivatives. Among the commonly used lubricants are magnesium stearate, paraffin wax, various metallic soaps and polyethylene glycol.

The method of the invention can also be practiced by the administration of the compound as a slow release bolus. Such boluses are made as tablets are made except that a means to delay the dissolution of the compound is provided. Boluses are made to release for lengthy periods. The slow dissolution is assisted by choosing a highly water-inslouble form of the compound. A substance such as iron filings is added to raise the density of the bolus and keep it static on the bottom of the rumen. Dissolution of the compound is delayed by use of a matrix of insoluble materials in which the drug is embedded. for example, substances such vegetable waxes, purified mineral waxes, and water-insoluble polymeric materials are useful.

Drenches of the compounds are prepared most easily by choosing a water-soluble form of the compound. If an insoluble form is desired for some reason, a suspension may be made. Alternatively, a drench may be formulated as a solution in a physiologically acceptable solvent such as a polyethylene glycol.

Suspensions of insoluble forms of the compounds can be prepared in nonsolvents such as vegetable oils such as peanut, corn, or sesame oil; in a glycol such as propylene glycol or a polyethylene glycol; or in water, depending on the form of the compound chosen.

Suitable physiologically-acceptable adjuvants are necessary in order to keep the compound suspended.

The adjuvants can be chosen from among the thickeners, such as carboxymethylcellulose, polyvinylpyrrolidone, gelatin, and the alginates. Many classes of surfactants serve to suspend the compounds of this invention. For example, lecithin, alkylphenol polyethylene oxide adducts, naphthalenesulfonates, alkylbenzenesulfonates, and the polyoxyethylene sorbitan esters are useful for making suspensions in liquid non-solvents.

In addition may substances which effect the hydrophilicity, density, and surface tension of the liquid can assist in making suspension in individual cases. For example, silicone anti-foams, glycols, sorbitol, and sugars can be useful suspending agents.

The suspendable compounds may be offered to the grower as a suspension, or as a dry mixture of the compounds and adjuvants to be diluted before use.

These compounds may also be administered in the drinking water of the ruminants. Incorporation into drinking water is performed by adding a water-soluble or water-suspendable form of the desired antibiotic to the water in the proper amount. Formulation of the compound for addition to drinking water follows the same principles as formulation fo drenches.

The most practical way to treat animals with the compounds of the invention is by the formulation of the compound into the feed supply. Any type of feed may be medicated with the compounds, including common dry feeds, liquid feeds, and pelleted feeds.

The methods of formulating drugs into animal feeds are well known. It is usual to make a concentrated drug premix as a raw material for medicated feeds. For example, typical drug premixes may contain from about 1 to about 400 grams of drug per pound of premix. The wide range results from the wide range of concentration of drug which may be desired in the final feed. Premixes may be either liquid or solid.

Generally the daily dosage of the compounds of this invention will be about 0.1 to 1.0 mg per kg body weight, preferably about 0.3 to 0.8 mg/kg. Thus, a 800 pound (about 360 kg) steer would receive about 36 to 360 mg and preferably about 109 to 290 mg.

The formulation of ruminant feeds containing the proper amount of the compounds for useful treatment is mainly a matter of arithmetic. It is necessary only to calculate the amount of compound which it is desired to administer to each animal, to take into account the amount of feed per day which the animal eats and the concentration of compound in the pre-mix to be used, and calculate the proper concentration of compound in the feed.

All of the methods of formulating, mixing, and pelleting feeds which are normally used in the ruminant feed art are entirely appropriate for manufacturing feeds containing the compounds of the method.

The compounds of this invention are also effective in controlling coccidial infections in warm blooded animal hosts. The animals in which these compounds are useful include ruminants such as cattle, sheep, and goats as well a non-ruminants such as horses, pigs, chickens and particularly young chicks. The means of administration is similar to that for the treatment of ruminants and preferably is given orally, particularly to young chicks in their feed. The dosages useful for treating coccidial infections are from 0.1 to 3.0 mg/kg.

The following examples set forth methods for preparing representative compounds of this invention and biological data for representative compounds of this invention. It is understood, of course, that the examples are not to be read as limiting the scope of the claimed subject matter, but are given by way of illustration of the preparation and use of the invention.

EXAMPLE 1

A. Crude laidlomycin (4.8 grams) is chromatographed on silica gel using ethylacetate as the eluant. Eluting with 1.0 liter of ethyl acetate and collecting the 400–700 ml fractions affords a solution of sodium laidlomycin in ethylacetate. Removing the ethyl acetate under vacuum affords sodium laidlomycin (2.2 grams) having a melting point of 259°–261° C., with an Rf of 0.5 using ethyl acetate.

A solution of 150 milligrams of sodium laidlomycin in 5 mls of pyridine is cooled to 5° C. and 100 milligrams of butyryl chloride is added. After three hours at 5° C., the mixture is taken into 25 mls of methylene chloride, washed with 25 mls of hydrochloric acid and 25 mls of brine, then dried over sodium sulfate. The methylene chloride solvent is removed under vacuum and the residue is chromatographed on silica gel using ethyl acetate. Eluting with 0.1 liter of ethyl acetate and collecting the 50–100 ml fractions gives 130 mgs of the monobutyrate of laidlomycin (Formula (A) where $R^1$ is $C(O)CH_2CH_2CH_3$ and $R^2$ is H), m.p. 77°–80° C. and further characterized by the Carbon-13 Magnetic Resonance (CMR) Data set forth in Table A.

B. By following in principle the above procedure but substituting other appropriate acid chlorides such as acetyl chloride, propionyl chloride, isobutyryl chloride, pentanoyl chloride, hexanoyl chloride, heptanoyl chloride, octanoyl chloride, decanoyl chloride, dodecanoyl chloride, stearyl chloride, cyclopropylcarbonyloxy chloride, cyclobutylcarbonyloxy chloride, cyclopentylcarbonyloxy chloride or cyclohexylcarbonyloxy chloride for butyryl chloride, the monoesters of laidlomycin (Formula (A) wherein $R^2$ is hydrogen and $R^1$ is an acyl group) are prepared as set forth below. In the following list, the parenthetical expression is the abbreviation for the compound shown, which abbreviation is later used in Table A to represent the compound.

laidlomycin acetate ($L.C_2$), m.p. 115° C.;
laidlomycin propionate ($L.C_3$), m.p. 65°–67° C.;
laidlomycin isobutyrate, m.p. 62°–65° C.;
laidlomycin pentanoate ($L.C_5$), m.p. 90°–93° C.;
laidlomycin hexanoate ($L.C_6$), m.p. 70°–73° C.;
laidlomycin heptanoate (oil), ir 1730 cm$^{-1}$;
laidlomycin octanoate (oil), ir 1730 cm$^{-1}$;
laidlomycin decanoate, m.p. 54°–56° C.;
laidlomycin dodecanoate (oil), ir 1730 cm$^{-1}$;
laidlomycin stearate ($L.C_{18}$); m.p. 43°–45° C.
laidlomycin cyclopropylcarboxylate (L.CPC), m.p. 85°–87° C.;
laidlomycin cyclobutylcarboxylate (L.CBC), m.p. 68°–70° C.;
laidlomycin cyclopentylcarboxylate, m.p. 32°–34° C.;
laidlomycin cyclohexylcarboxylate; and the like.

Selected compounds are further characterized with CMR Data in Table A. In numbering the carbons in the laidlomycin molecule, and esters thereof, the following convention was employed:

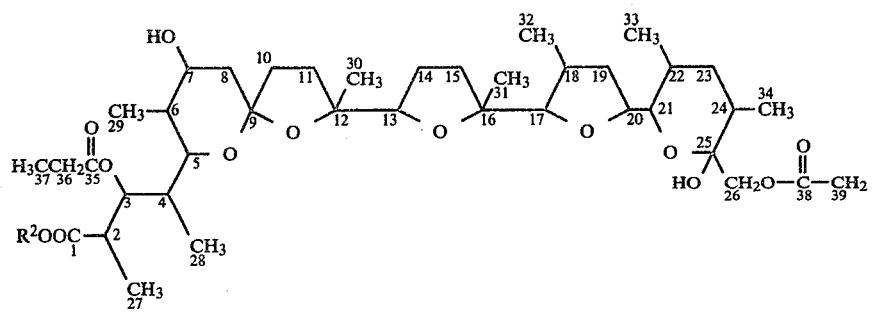

Carbons C-1, C-7, C-26, C-35, C-38 and C-39 were chosen as best distinguishing the compounds of this invention from the parent. In the column under C-39..., the numbers are given which correspond to the acetate (C-39), the propionate (C-39, C-40), the butyrate (C-39, C-40, C-41), etc. Only the clearly identified peaks are chosen. Thus, in identifying the stearate only six peaks are set forth even though the stearate has 18 carbons.

TABLE A
CMR DATA
(PPM from tetramethylsilane)[1]

| COMPOUND | C-1 | C-7 | C-26 | C-35 | C-38 | C-39 |
|---|---|---|---|---|---|---|
| NaL. | 180.26 | 70.64 | 64.92 | 173.83 | — | — |
| L.C$_2$ | 180.85 | 70.45 | 64.34 | 173.86 | 171.03 | 21.03 |
| L.C$_3$ | 180.85 | 70.61 | 63.84 | 173.93 | 174.41 | 9.01, 27.56 |
| L.C$_4$ | 180.72 | 70.61 | 63.78 | 173.76 | 173.47 | 13.84, 18.21, 36.15 |
| L.CPC | 180.75 | 70.51 | 63.52 | 173.89 | 174.93 | 7.77, 8.42, 12.81 |
| L.C$_5$ | 180.85 | 70.51 | 63.81 | 173.92 | 173.92 | 13.82, 22.33, 27.96, 33.97 |
| L.CBC | 180.78 | 70.54 | 63.42 | 173.89 | 175.29 | 18.50, 24.67, 25.65, 38.17 |
| L.C$_6$ | 180.85 | 70.51 | 63.85 | 173.70 | 173.86 | 13.91, 22.43, 24.51, 31.37, 34.26 |
| L.C$_{18}$ | 180.82 | 70.51 | 63.78 | 173.73 | 173.89 | 14.14, 22.72, 24.58, 29.49, 29.71, 33.71 |

[1]Solvent: CDCl$_3$ treated with K$_2$CO$_3$—D$_2$O using a Bruker 90 instrument.

EXAMPLE 2
BIOLOGICAL ACTIVITY

Enhancement of intraruminal propionic acid production is determined using a batch culture fermentation system. Rumen contents from a rumen-fistulated bovine are mixed with an equal amount of buffer which contains mineral, energy and nitrogen sources required for continued growth and metabolism of the mixed microbial population. Aliquots of this inoculum then are transferred to incubation vessels containing appropriate amounts of sodium laidlomycin (Na L.) (see Example 1A), and L. butyrate (L.C$_4$) (prepared according to the procedure of Example 1A). After 9 hours of incubation at 39° C., concentrations of individual volatile fatty acids in each incubation vessel are determined by gas-liquid chromatography. The net production of each individual volatile fatty acid (acetic [AA], propionic [PA] and butyric [BA]) is calculated as the difference between the concentration after incubation and the concentration before incubation. The molar percentage of propionic acid produced is calculated from the following equation:

$$\% \text{ propionic acid} = \frac{PA}{AA + PA + BA} \times 100$$

Inhibition of lactic acid accumulation is determined using a second batch culture fermentation system. Rumen contents from a rumen fistulated bovine are mixed with an equal amount of buffer which contains a 150 mM concentration of glucose. Following 6 hours of incubation at 39° C., lactic acid produced in the fermentation is analyzed by a specific enzymatic assay. The concentration of lactic acid in the fermentation broth is quantified by the increase in absorbance of light at 340 mm when nicotinamide adenine dinucleotide is reduced by lactic acid with the aid of lactate dehydrogenase.

The comparative activities of sodium laidlomycin (Na L.) and the laidlomycin butyrate upon propionic acid and lactic acid production are set forth in Tables 1 and 2 where the concentration is in micrograms per ml (μg/ml).

TABLE 1

| Concentration of Test Compound (μg/ml) | % Propionic Acid | |
|---|---|---|
| | Na L. | L. C$_4$ |
| 10 | 45.4 | 53.9 |
| 5 | 44.4 | 49.3 |
| 2.5 | 43.2 | 52.2 |
| 1.25 | 41.3 | 46.1 |
| .62 | 40.8 | 46.4 |
| .31 | 40.2 | 43.6 |
| 0 | 35.4 | 35.4 |

TABLE 2

| Concentration of Test Compound (μg/ml) | Lactic Acid Accumulation (% of Control) | |
|---|---|---|
| | Na L. | L. C$_4$ |
| 10 | 67 | 13 |
| 5 | 93 | 13 |
| 2.5 | 112 | 11 |
| 1.25 | 125 | 8 |
| .62 | 132 | 30 |
| .31 | 135 | 71 |
| 0 | 100 | 100 |

From the results of these tests it is clear that the butyrate of laidlomycin demonstrates a surprisingly increased potency toward both enhancement of propionic acid production and inhibition of lactic acid accumulation.

EXAMPLE 3

BIOLOGICAL ACTIVITY

The procedure of Example 2 was followed to compare laidlomycin (L.), sodium L. (Na L.), L.-propionate (L.$C_3$), L. butyrate (L.$C_4$), L. isobutyrate (L. iso$C_4$), L. pentanoate (L.$C_5$) and L. hexanoate (L.$C_6$). The results are set forth in Tables 2 and 3.

TABLE 3

| Concentration of Test Compound ($\mu$g/ml) | % Propionic Acid | | | | | | |
|---|---|---|---|---|---|---|---|
| | L. | Na L. | L. $C_4$ | L. iso $C_4$ | L. $C_5$ | L. $C_6$ | L. $C_3$ |
| 20 | 43.2 | 36.8 | 46.9 | 47.5 | 39.7 | 41.7 | 44.4 |
| 5 | 39.8 | 34.6 | 43.7 | 43.9 | 36.1 | 40.1 | 41.9 |
| 1.25 | 36.0 | 34.1 | 39.9 | 39.6 | 33.9 | 37.1 | 37.8 |
| .31 | 32.1 | 32.0 | 35.5 | 34.3 | 30.6 | 33.0 | 32.9 |
| 0 | 28.5 | 28.5 | 28.5 | 28.5 | 28.5 | 28.5 | 28.5 |

TABLE 4

| Concentration of Test Compound ($\mu$g/ml) | Accumulation of Lactic Acid - % of Control | | | | | | |
|---|---|---|---|---|---|---|---|
| | L. | Na L. | L. $C_4$ | L. iso $C_4$ | L. $C_5$ | L. $C_6$ | L. $C_3$ |
| 20 | 16 | 40 | 19 | 16 | 11 | 14 | 14 |
| 5 | 20 | 57 | 15 | 13 | 13 | 11 | 13 |
| 1.25 | 83 | 94 | 13 | 12 | 54 | 18 | 14 |
| .31 | 121 | 114 | 38 | 37 | 109 | 60 | 71 |
| 0 | 100 | 100 | 100 | 100 | 100 | 100 | 100 |

EXAMPLE 4

The procedure of Example 2 was followed to compare the activities of L. heptanoate (L. $C_7$), L. octanoate (L. $C_8$), L. decanoate (L. $C_{10}$) and L. dodecanoate (L. $C_{12}$) in increasing propionic acid production and inhibiting lactic acid production. The results are set forth in Tables 5 and 6.

TABLE 5

| Concentration of Test Compound ($\mu$g/ml) | % Propionic Acid | | | |
|---|---|---|---|---|
| | L. $C_7$ | L. $C_8$ | L. $C_{10}$ | L.$C_{12}$ |
| 20 | 47.2 | 49.4 | 48.1 | 48.0 |
| 10 | 48.1 | 47.5 | 46.6 | 47.7 |
| 5 | 48.4 | 48.2 | 46.7 | 46.8 |
| 2.5 | 46.9 | 47.3 | 47.1 | 46.1 |

TABLE 5-continued

| Concentration of Test Compound ($\mu$g/ml) | % Propionic Acid | | | |
|---|---|---|---|---|
| | L. $C_7$ | L. $C_8$ | L. $C_{10}$ | L.$C_{12}$ |
| 1.25 | 46.2 | 46.4 | 45.5 | 45.3 |
| .63 | 45.3 | 43.9 | 43.6 | 43.8 |
| .31 | 41.4 | 42.7 | 39.9 | 42.0 |
| 0 | 35.5 | 35.5 | 35.5 | 35.5 |

TABLE 6

| Concentration of Test Compound ($\mu$g/ml) | Lactic Acid Accumulation ($\mu$mol/ml) | | | |
|---|---|---|---|---|
| | L. $C_7$ | L. $C_8$ | L. $C_{10}$ | L. $C_{12}$ |
| 20 | 1.94 | 2.14 | 0.96 | 1.65 |
| 10 | 1.46 | 1.39 | 0.94 | 2.16 |
| 5 | 1.16 | 1.27 | 0.94 | 3.32 |
| 2.5 | 1.32 | 1.31 | 1.20 | 1.04 |
| 1.25 | 1.90 | 1.21 | 0.84 | 11.19 |
| .63 | 14.12 | 9.41 | 30.78 | 38.01 |
| .31 | 38.37 | 41.96 | 36.86 | 34.90 |
| 0 | 36.65 | 36.65 | 36.65 | 36.65 |

EXAMPLE 5

The procedure of Example 2 was followed to compare the activities of laidlomycin (L.) acetate (L. $C_2$), L. pentanoate (L. $C_5$), L. stearate (L. $C_{18}$), L. cyclobutylcarboxylate, L. cyclopentylcarboxylate, L. cyclohexylcarboxylate and L. cyclopropylcarboxylate. The results are set forth in Tables 7 and 8.

TABLE 7

| Concentration of Test Compound ($\mu$g/ml) | % Propionic Acid | | | | | | |
|---|---|---|---|---|---|---|---|
| | L. $C_2$ | L. $C_5$ | L. $C_{18}$ | (Cyclobutyl-carboxylate) | (Cyclopentyl-carboxylate) | (Cyclohexyl-carboxylate) | (Cyclopropyl-carboxylate) |
| 20 | 53.0 | 51.1 | 45.8 | 51.2 | 50.0 | 53.3 | 50.7 |
| 10 | 51.2 | 51.6 | 45.5 | 51.8 | 51.6 | 51.8 | 49.6 |
| 5 | 52.2 | 49.9 | 44.6 | 51.7 | 51.1 | 51.6 | 50.9 |
| 2.5 | 50.4 | 50.9 | 41.6 | 52.5 | 50.3 | 50.8 | 49.3 |
| 1.25 | 50.7 | 48.7 | 40.0 | 50.0 | 51.9 | 50.1 | 49.7 |
| .625 | 47.1 | 48.1 | 37.6 | 47.1 | 47.9 | 49.0 | 46.4 |
| .313 | 42.8 | 45.9 | 37.1 | 47.5 | 47.1 | 47.2 | 47.7 |
| 0 | 36.1 | 36.1 | 36.1 | 36.1 | 36.1 | 36.1 | 36.1 |

TABLE 8

| Concentration of Test Compound (µg/ml) | Lactic Acid Accumulation (µmol/ml) | | | | | | |
|---|---|---|---|---|---|---|---|
| | L. C$_2$ | L. C$_5$ | L. C$_{18}$ | (Cyclobutyl-carboxylate) | (Cyclopentyl-carboxylate) | (Cyclohexyl-carboxylate) | (Cyclopropyl-carboxylate) |
| 20 | 5.28 | 5.13 | 29.93 | 4.75 | 9.66 | 5.72 | 3.96 |
| 10 | 4.35 | 4.63 | 37.83 | 4.73 | 4.53 | 4.97 | 3.53 |
| 5 | 4.35 | 4.04 | 46.20 | 4.32 | 4.08 | 4.83 | 3.17 |
| 2.5 | 4.34 | 3.75 | 52.51 | 4.01 | 3.73 | 4.40 | 3.16 |
| 1.25 | 6.89 | 4.67 | 48.87 | 3.82 | 3.63 | 3.74 | 2.50 |
| .625 | 22.23 | 11.91 | 52.57 | 8.05 | 6.79 | 12.78 | 2.12 |
| .313 | 41.19 | 24.62 | 50.29 | 23.25 | 24.75 | 35.55 | 15.54 |
| 0 | 40.47 | 40.47 | 40.47 | 40.47 | 40.47 | 40.47 | 40.47 |

EXAMPLE 6

Five groups of male, Swiss-Webster mice (Simonsen), each mouse weighing about 25 grams, were dosed orally with 0.25 ml of a solution of laidlomycin butyrate in sesame oil. A control group of six mice received only sesame oil. The mice were observed daily for mortality for 21 days. The dosage and results are set forth in Table 9, below. From this information the LD$_{50}$ as calculated to be more than 200 mg/kg.

TABLE 9

| Group | No. Mice | Dosage (mg/kg) | No. Deaths/No. Mice |
|---|---|---|---|
| 1 | 6 | 0 | 0/6 |
| 2 | 6 | 12.5 | 0/6 |
| 3 | 6 | 25 | 0/6 |
| 4 | 6 | 50 | 0/6 |
| 5 | 6 | 100 | 0/6 |
| 6 | 6 | 200 | 0/6 |

Other compounds of this invention show similar toxicity characteristics.

EXAMPLE 7

A premix formulation of the composition set forth in Table 10 is prepared as set forth below.

TABLE 10

| Component | % weight |
|---|---|
| Laidlomycin butyrate | 12.0 |
| Ethoxyquin | 0.01 |
| Rice Mill Hulls | 87.99 |

The ethoxyquin is mixed with 1.2% of the rice mill hulls to prepare an initial premix composition. This mixture is then thoroughly mixed with the remainder of the rice mill hulls whereupon the L. butyrate is added and thoroughly mixed to prepare the final formulation.

EXAMPLE 8

Three hundred twenty (320) g of the sodium salt of laidlomycin is mixed with 6.4 l of methylene chloride (CH$_2$Cl$_2$) and 215 ml triethylamine (TEA) then cooled with stirring to $-10°$ C. under nitrogen. One hundred four (104) ml butyrylchloride (BuCl) is added over a twelve minute span as the temperature rises to $-5°$ C. Over ten minute intervals six additions are made to the reaction vessel, with each addition being 15.4 ml TEA and subsequently 11.5 ml BuCl. The resulting reaction mixture is extracted twice with 2 l portions of aqueous NaHCO$_3$, once with a 2 l portion of water, twice with 2 l portions of 10% HCl, twice with 2 l portions of water and once with a 2 l portion of saturated brine. The organic phase is dried over Na$_2$SO$_4$, the solvent removed in vacuo, and the resulting oil is seeded, then stored overnight at $-10°$ C. The resulting precipitate is slurried with 250 ml of 20% ether/hexane, 250 ml of hexane is added, and the mixture is cooled to $-10°$ C. for one hour then filtered to give 242.8 g of a product having a mp of 104°-106° C. (Product A). The solvents from the mother liquor are then concentrated to give another precipitate which is similarly treated with ether/hexane to give 73.4 g of a product having a mp of 93-96 (Product B). The solvents are removed from the mother liquor and 25 g KHCO$_3$ in 100 ml water, along with one l of methanol (MeOH) is added thereto. Four hundred ml of water is added to cause an oil to form. The oil is redissolved by adding 500 ml MeOH and the mixture is allowed to stand for two days; no precipitate forms. Two hundred (200) ml of water are added and the mixture is filtered to remove insolubles. Twenty-five (25) g of KHCO$_3$ is added to the filtrate and a precipitate forms within an hour. The mixture is stirred for two and a half days then filtered to give a product which, when dried, exhibits a mp of 133°-136° C. (Product C).

A mixture of 222.8 g of product A, 72.8 g of product B, and 29.1 g of product C is mixed with 1.5 l acetone, 75 g KHCO$_3$ and 150 ml water. Twenty-five (25) g of KHCO$_3$ is added after 30 minutes and another 25 g after another 30 minutes. The acetone is removed in vacuo and 500 ml MeOH added thereto. The resulting mixture is concentrated and 1.5 l of MeOH and 600 ml water is added thereto to give a precipitate. The mixture is transferred to another vessel, slurrying with extra aqueous MeOH and stirred for one hour. The precipitate is collected, washed 4 times with 250 ml of water, suctioned dry, and dried overnight in an oven to give 273.9 of the potassium salt of laidlomycin butyrate (Formula (A)) where R$^1$ is C(O)CH$_2$CH$_2$CH$_3$ and R$^2$ is K), mp 143°-148° C.

The subject matter claimed is:

1. A compound chosen from those represented by the Formula

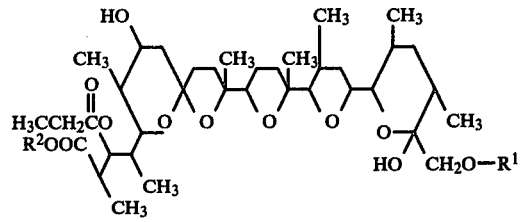

wherein R$^1$ is an aliphatic acyl group of 2 to 12 carbon atoms or an alicyclic hydrocarbon acyl group of 4 to 9 carbon atoms and $R^2$ is an alkali metal cation or hydrogen.

2. A compound of claim 1 wherein $R^1$ is an aliphatic acyl of 3–6 carbon atoms and $R^2$ is hydrogen, sodium or potassium.

3. A compound of claim 2 wherein $R^1$ is aliphatic acyl of 3 or 4 carbon atoms.

4. A compound of claim 3 wherein $R^1$ is

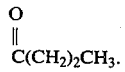

5. A method of increasing the efficiency of food utilization in a ruminant animal having a developed rumen function which comprises the oral administration to such animal of a propionate-increasing amount of a compound of claim 1.

6. The method of claim 5 wherein $R^1$ is aliphatic acyl of 3–6 carbon atoms and $R^2$ is hydrogen, sodium or potassium.

7. The method of claim 6 wherein $R^1$ is aliphatic acyl of 3 or 4 carbon atoms.

8. The method of claim 7 wherein $R^1$ is

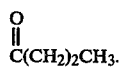

9. A veterinary pharmaceutical composition which comprises a compound of claim 1 in combination with a suitable feed carrier wherein said compound is present in an amount sufficient to provide a daily dose of between 0.1 to 3.0 mg/kg/body weight.

10. A composition for increasing the efficiency of feed utilization of a ruminant animal having a developed rumen function which comprises a compound of claim 1 in combination with a pharmaceutically acceptable veterinary excipient.

11. Aliphatic and alicyclic ($C_2$–$C_{18}$)acylated laidlomycin compounds wherein
the acetate of laidlomycin has a melting point of 115° C. and has CMR data showing clearly identified peaks at 180.85, 70.45, 64.34, 173.86, 171.03, and 21.03 (in PPM from tetramethylsilane using as a solvent $CDCl_3$ treated with $K_2CO_3$-$D_2O$;

the butyrate of laidlomycin has a melting point of 77°–80° C. and has CMR data showing clearly identified peaks at 180.72, 70.61, 63.78, 173.76, 173.47, 13.84, 18.21, and 36.15 (in PPM from tetramethylsilane using as a solvent $CDCl_3$ treated with $K_2CO_3$-$D_2O$);

the decanoate of laidlomycin has a melting point of 54°–66° C.;

the stearate of laidlomycin has a melting point of 43°–45° C. and has CMR data showing clearly identified peaks at 180.82, 70.51, 63.78, 173.73, 173.89, 14.14, 22.72, 24.58, 29.49, 29.71 and 33.71 (in PPM from tetramethylsilane using as a solvent $CDCl_3$ treated with $K_2CO_3$-$D_2O$);

the cyclopropylcarboxylate of laidlomycin has a melting point of 85°–87° C. and has CMR data showing clearly identified peaks at 180.75, 70.51, 63.52, 173.89, 174.93, 7.77, 8.42, and 12.81 (in PPM from tetramethylsilane using as a solvent $CDCl$ treated with $K_2CO_3$-$D_2O$); and the cyclopentylcarboxylate of laidlomycin has a melting point of 32°–34° C.

12. A feed premix for medicating feed which comprises 1 to 400 grams of a compound according to claim 1 per pound of premix.

13. A compound according to claim 3 wherein $R^1$ is n-propionate, which is the compound laidlomycin propionate.

14. A compound which is an acylated aliphatic or alicyclic laidlomycin derivative wherein said aliphatic acyl group has 2 to 12 carbon atoms or the alicyclic hydrocarbon acyl group has 4 to 9 carbon atoms prepared by a process which comprises reacting laidlomycin or an alkali metal salt thereof at 0° to 30° C. with a corresponding alithatic or alicyclic carboxcyclic acid halide or anhydride to form said laidlomycin derivative.

* * * * *

UNITED STATES PATENT AND TRADEMARK OFFICE

CERTIFICATE EXTENDING PATENT TERM
UNDER 35 U.S.C. § 156

PATENT NO.      : 4,431,665

DATED           : February 14, 1984

INVENTOR(S)     : Arthur Kluge et al.

PATENT OWNER    : Syntex (U.S.A.) Inc.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

THREE YEARS with all rights pertaining thereto as provided by 35 U.S.C. § 156(b).

I have caused the seal of the Patent and Trademark Office to be affixed this 23rd day of January 1996.

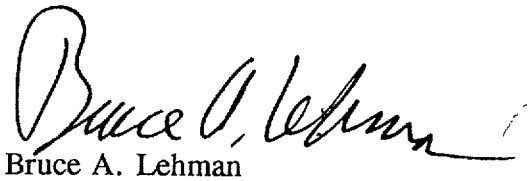

Bruce A. Lehman
Assistant Secretary of Commerce and
Commissioner of Patents and Trademarks